United States Patent
Rosiello

(10) Patent No.: US 8,133,165 B2
(45) Date of Patent: *Mar. 13, 2012

(54) EXPANDABLE PROCESSING AND EXPRESSION CHAMBER

(75) Inventor: Keith M. Rosiello, Shrewsbury, MA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/651,800

(22) Filed: Jan. 4, 2010

(65) Prior Publication Data
US 2010/0197476 A1    Aug. 5, 2010

Related U.S. Application Data

(63) Continuation of application No. 10/633,842, filed on Aug. 4, 2003, now Pat. No. 7,651,457.

(51) Int. Cl.
*B04B 7/08*    (2006.01)
(52) U.S. Cl. .................. 494/34; 494/45; 92/34
(58) Field of Classification Search .......... 494/34, 494/45; 92/34, 37; 220/672
See application file for complete search history.

(56) References Cited

U.S. PATENT DOCUMENTS

| | | |
|---|---|---|
| 781,939 A | 2/1905 | Fulton |
| 988,854 A | 4/1911 | Bixler |
| 1,007,451 A | 10/1911 | Kitts |
| 2,000,890 A | 6/1932 | Hueber et al. |
| 2,341,556 A | 2/1944 | Joy |
| 2,657,074 A | 10/1953 | Schwester et al. |
| 2,686,006 A | 8/1954 | Hasselquist |
| 2,920,656 A | 1/1960 | Bertolet, Jr. |
| 3,019,820 A | 2/1962 | Yowell et al. |
| 3,503,326 A | 3/1970 | Juhasz et al. |
| 3,561,672 A | 2/1971 | Schlutz et al. |
| 3,724,497 A | 4/1973 | Federer et al. |
| 4,053,416 A | 10/1977 | Howard et al. |
| 4,113,173 A | 9/1978 | Lolachi |
| 4,379,051 A | 4/1983 | Hiesinger et al. |
| 4,491,519 A | 1/1985 | Kurita |
| 4,564,359 A | 1/1986 | Ruhlang |
| 4,610,369 A | 9/1986 | Mercier |
| 4,984,970 A | 1/1991 | Eickmann |
| 5,019,255 A | 5/1991 | Dahlquist et al. |
| 5,242,398 A | 9/1993 | Knoll et al. |
| 5,547,591 A | 8/1996 | Hagihara et al. |
| 5,690,815 A | 11/1997 | Krasnoff et al. |
| 5,733,253 A | 3/1998 | Headley et al. |
| 6,149,806 A | 11/2000 | Baer |
| 6,175,420 B1 | 1/2001 | Barry et al. |
| 6,387,282 B1 | 5/2002 | Heckl et al. |
| 7,651,457 B2 * | 1/2010 | Rosiello .................. 494/34 |

(Continued)

FOREIGN PATENT DOCUMENTS

EP    0 405 094    10/1995

(Continued)

*Primary Examiner* — David Sorkin
(74) *Attorney, Agent, or Firm* — Pierce Atwood LLP; Joseph M. Maraia

(57) ABSTRACT

A flexible processing and/or expressor chamber for a biological cell processing apparatus is provided which may include a first side and a second side and having a expandable wall, wherein a first end of the expandable wall is attached to a circumference of the first side of the flexible chamber and a second end of the expandable wall is attached to a circumference of the second side of the flexible chamber. Either or both sides of the chamber may include an axial opening.

18 Claims, 4 Drawing Sheets

U.S. PATENT DOCUMENTS

| | | |
|---|---|---|
| 2002/0020680 A1 | 2/2002 | Jorgensen |
| 2002/0082153 A1 | 6/2002 | Jorgensen et al. |

FOREIGN PATENT DOCUMENTS

| | | |
|---|---|---|
| FR | 2487672 | 2/1982 |
| WO | WO 88/06922 | 9/1988 |
| WO | WO 92/00145 | 1/1992 |
| WO | WO 98/52629 | 11/1998 |
| WO | WO 01/30505 | 5/2001 |
| WO | WO 02/28451 | 4/2002 |
| WO | WO 03/024510 | 3/2003 |

* cited by examiner

EXPANDABLE PROCESSING AND EXPRESSION CHAMBER

CROSS-REFERENCE TO RELATED PATENT APPLICATIONS

This application is a continuation application of U.S. application Ser. No. 10/633,842, now U.S. Pat. No. 7,651,457, filed Aug. 4, 2003, which is related to co-pending U.S. patent application Ser. No. 09/970,547, filed Oct. 3, 2001, entitled, "MULTIPLE PROCESSING CHAMBER SET AND USE THEREOF, co-pending U.S. patent application Ser. No. 10/232,197, filed Aug. 28, 2002, entitled, "BLOOD PRODUCT TRANSFER SYSTEM"; and co-pending U.S. patent application Ser. No. 10/211,143, filed Aug. 2, 2002, entitled, "PROCESSING BAG FOR COMPONENT SEPARATOR SYSTEM AND METHOD OF REMOVING SEPARATED COMPONENTS". Each of the foregoing disclosures, in their entirety, is incorporated herein by reference.

BACKGROUND OF THE INVENTION

1. Field of the Invention

The invention relates to processing and/or expressor chambers for a material processing device, and more particularly to a flexible processing/expressor chamber/bag for a biological material, centrifugal processing device.

2. Background of the Invention

Flexible processing chambers (e.g., bags) for processing biological cells in a fixed volume centrifuge, and methods for use of such processing bags, e.g., by centrifugation, are known. For example, PCT patent application PCT/US98/10406 describes a flexible cell processing chamber having a rotating seal to keep the contents of the chamber sterile during processing. Flexible processing chambers advantageously are disposable and thus suitable for single-use sterile applications.

For certain applications, such as blood processing including blood component separation, enzymatic conversion of blood type, and pathogen inactivation of blood components, multiple units of material (e.g., blood) are processed at a time, in a single instrument under the same conditions. Co-pending, and jointly assigned U.S. patent application Ser. No. 09/970,547, discloses simultaneous processing of multiple processing chambers/bags which reduce the time and expense required to perform separation and conversion using only a single bag.

SUMMARY OF THE INVENTION

Embodiments of the present invention provide a novel expandable/collapsible processing and/or expressor bag for material (e.g., biological or otherwise) processing (for example) in a centrifugal or other processing device.

Accordingly, in a first embodiment of the present invention, a flexible chamber is provided which may include a first side and a second side and having a circumferential expandable wall. A first end of the expandable wall may be attached to a circumference of the first side of the flexible chamber and a second end of the expandable wall may be attached to a circumference of the second side of the flexible chamber.

In other embodiments of the present invention, a processing apparatus and/or a continuous flow centrifuge, may include one or more flexible chambers according to the above embodiment. Such a processing apparatus and/or continuous flow centrifuge may be a biological cell processing apparatus for processing, for example, blood of a human or an animal.

These and other aspects of the invention will be described in connection with the drawings and the detailed description below.

DETAILED DESCRIPTION OF THE EMBODIMENTS

Figure 1:
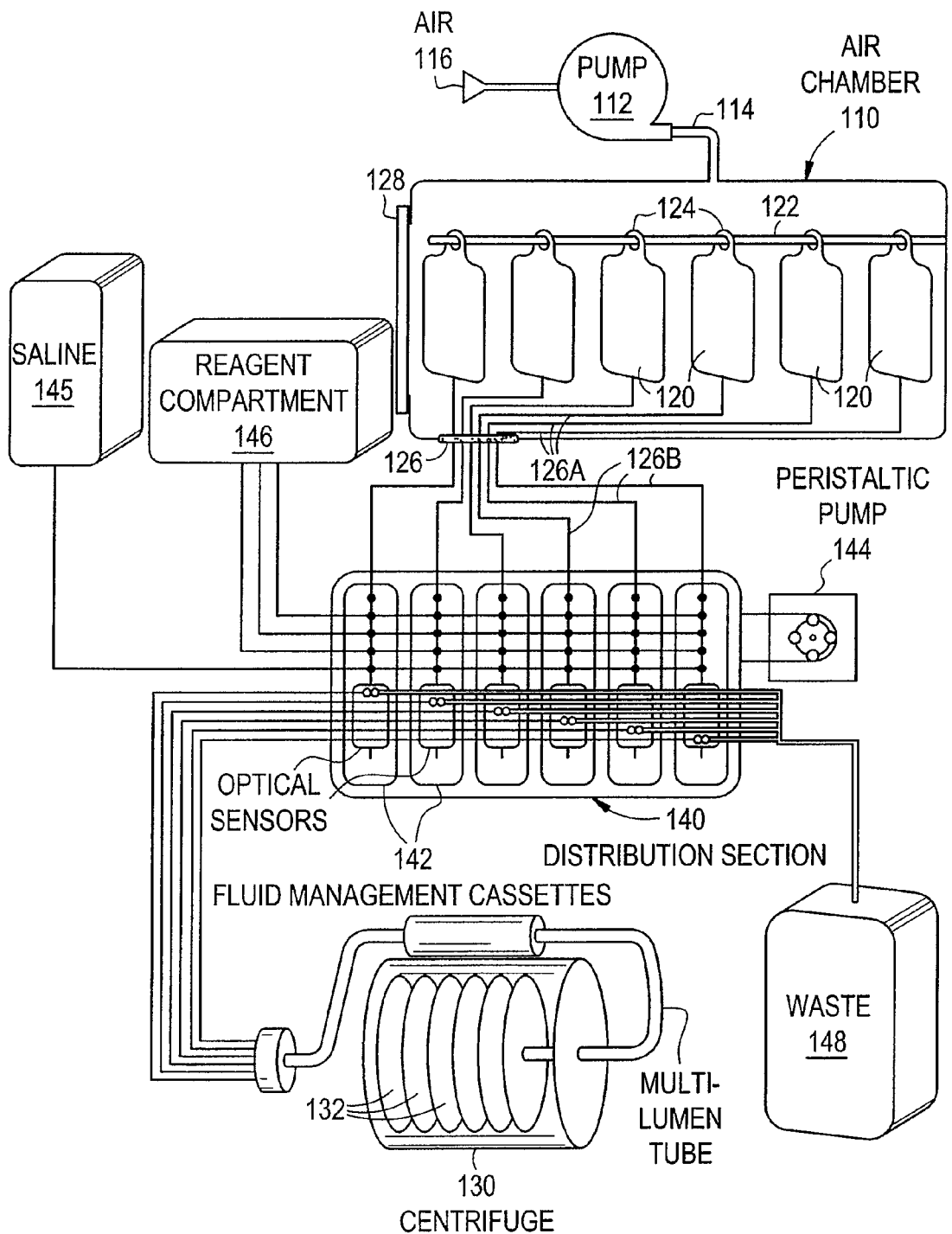
FIG. 1 illustrates an example of a centrifugal processing apparatus for use with one or more flexible processing/expressor chambers according to some embodiments of the present invention.

FIG. 1 illustrates a block diagram of an exemplary processing system embodying an exemplary device for processing biological cells (e.g., blood). Blood product, for example, is transferred from at least one blood storage bag to a centrifuge for processing. Reference is made to U.S. Pat. No. 6,175,420 to Barry et al., granted Jan. 16, 2001 for a more comprehensive description of the processes and devices employed by such a system. Reference may also be made to U.S. Pat. No. 5,665,048 to Jorgensen, granted Sep. 9, 1997 for further descriptions relating to the centrifuge itself. Both foregoing patents are incorporated herein by reference, in their entirety.

Although embodiments of the present invention may be used with a biological/blood processing apparatus, the embodiments are equally applicable to other uses separate and apart from biological material processing, and/or separate and apart from centrifugal processing.

Accordingly, FIG. 1 illustrates one device and process which enables the transfer a blood product to the centrifuge using, for example, air pressure, as disclosed in co-pending and jointly owned U.S. patent application Ser. No. 10/232, 197, filed Aug. 28, 2002, the entire disclosure of which is herein incorporated by reference. In this example, an airtight vacuum/pressure chamber 110 is coupled to an associated pump 112 by way of the tubing 114, which pumps or expels air from source 116 (e.g. ambient air). Within the chamber 110 are a series of blood product storage bags 120. Each of these bags is supported from a hanger 122 by means of a securing loop 124 associated with each bag. Individual lines or tubing from each bag 126A, 126B couples through the wall of the chamber by way an airtight fixture 126, positioned at the bottom of the chamber 110.

The processing device also includes a centrifuge 130 having one or more associated centrifuge processing bags 132 (which may also include expressor bags) and a distribution section 140 comprising a plurality of fluid management cassettes 142 and a peristaltic pump 144. Also coupled to the cassettes 142 is a saline supply or bag 145 and reagent compartment 146, and a waste bag 148 relating to the fluid management cassettes. Not specifically illustrated in FIG. 1, but considered as part of the system, is a computer controller which controls the operation of the device and processing of material.

The flexible chamber/bag according to the present invention may provide multiple and/or expandable processing and chamber sets for processing simultaneously and independently a number of separate samples at one time in a centrifugal cell processing device (for example). The multiple processing chamber sets permit sterile addition and removal of samples (and processed fractions thereof), processing fluids (including enzymes, salts, buffers and other process chemicals), and waste products without the need for rotating seals of any kind. Thus, the multiple processing chamber set represents a portion of a closed system for biological cell processing and includes a number of separate closed containers that can be treated in series or in parallel. Further details of such a system may be found in co-pending and jointly assigned U.S. patent application Ser. No. 09/970,547 (the '547 application), the entire disclosure of which is also incorporated by reference.

Figure 2A:
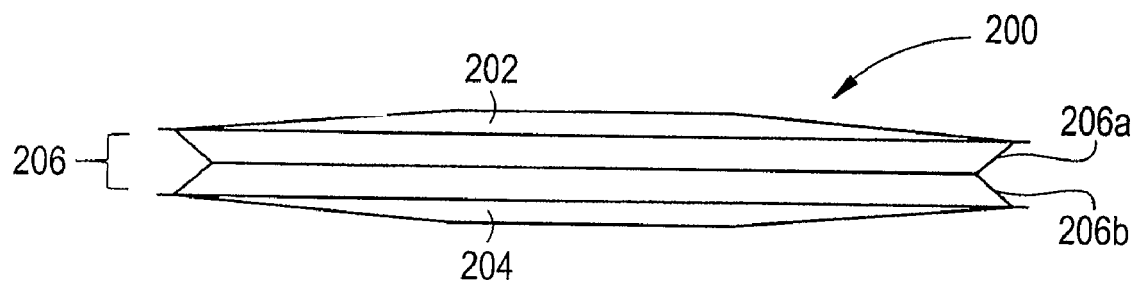
FIG. 2A illustrates a side view of a flexible processing/expressor chamber according to one embodiment of the present invention.
Figure 2B:
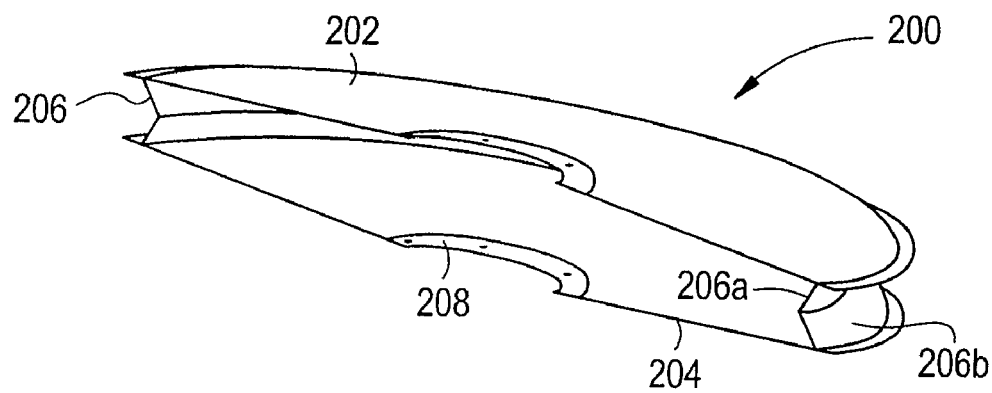
FIG. 2B illustrates a cross-sectional, perspective view of a flexible processing/expressor chamber according to the embodiment of the present invention shown in FIG. 2A.

As shown in FIGS. 2A and 2B, a processing or expressor bag 200, according to embodiments of the present invention, may include a first side 202 and a second side 204 connected to the first side circumferentially via an expandable/collapsible wall 206. The expandable wall may include a pair of partitions for allowing an adjustable wall length. In that regard, a partition pair may include a first partition 206a, which includes one end attached to the circumference of the first side 202, and a second linked partition 206b attached to the circumference of the second side 204.

Figure 3:
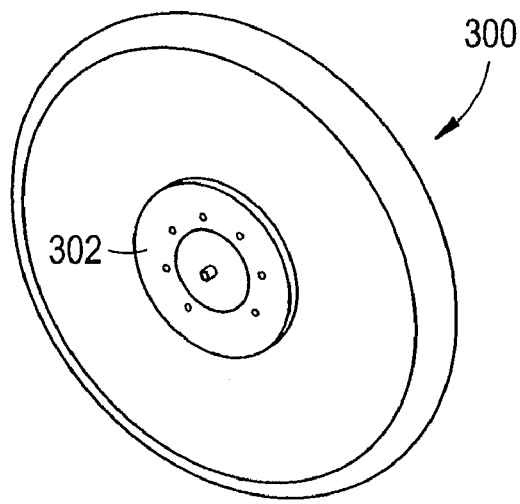
FIG. 3 illustrates a side, perspective view of a flexible processing/expressor chamber according to another embodiment of the present invention.

As also shown in FIGS. 2A and 2B, each side may include an axial opening for housing a central hub. The hub may be used so that multiple processing/expressor bags may be assembled together. An example of such a hub may be found in the '547 application. In that regard, FIG. 3 illustrates an example of a processing bag 300 having a hub 302 provided in the axial opening on at least one side of the bag.

Figure 4:
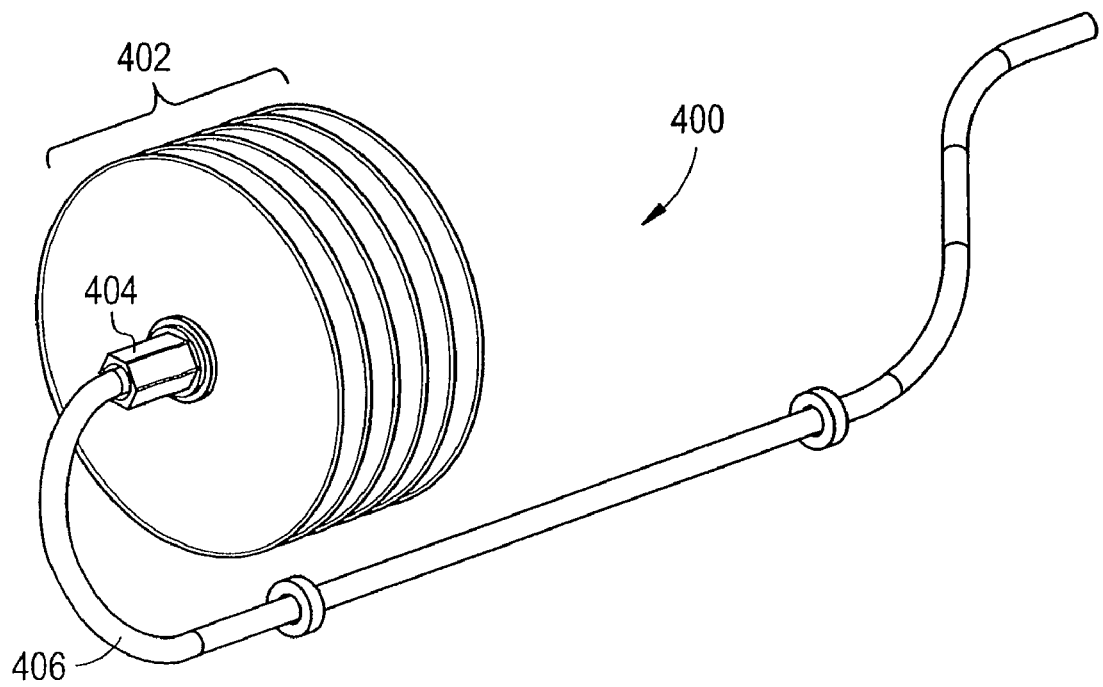
FIG. 4 illustrates a processing/expressor chamber assembly according to another embodiment of the present invention.
Figure 5A:
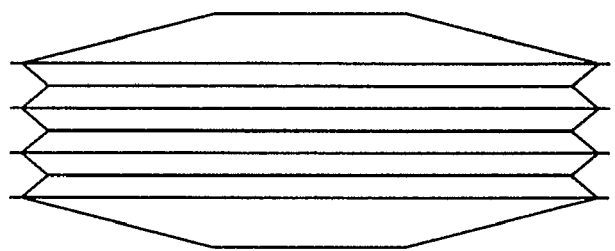
FIG. 5A is a side view of a processing/expressor chamber according to yet another embodiment of the present invention.
Figure 5B:
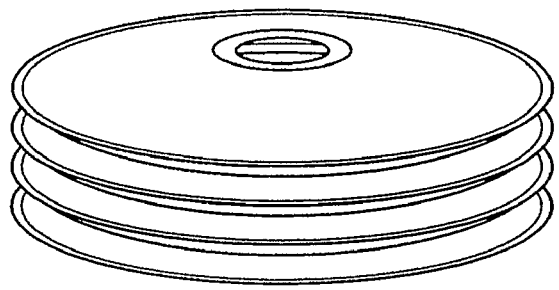
FIG. 5B is a perspective view of the processing/expressor chamber of the embodiment of the invention illustrated in FIG. 5A.
Figure 5C:
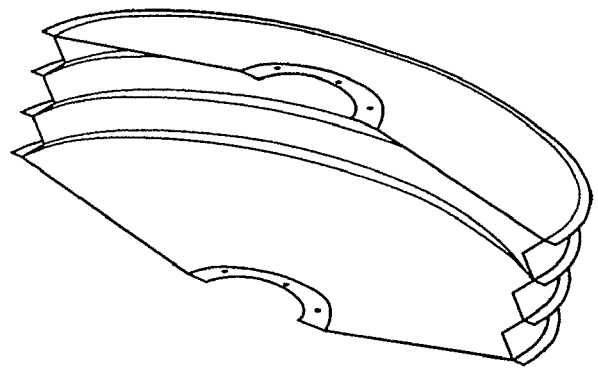
FIG. 5C is a cross-sectional, perspective view of the processing/expressor chamber of the embodiment of the invention illustrated in FIGS. 5A and 5B.

The hub allows multiple bags to be assembled together so that biological and/or other material sent to one or more processing bags may processed and expressed out of the centrifuge via the use of one or more expressor bags. In that regard, the '547 application discloses one or more arrangements of processing bags and expressor bags for processing. For example, FIG. 4 illustrates an assembly 400 of processing/expressor bags 402, coupled via coupling 404 to a multi-lumen line 406 (for example), so that fluids may be directed into and out of either or both of one or more of the processing bags and/or expressor bags. An example of such a multi-lumen line is disclosed in co-pending U.S. patent application Ser. No. 10/111,568, filed Oct. 27, 2000, entitled "CIRCUMFERENTIALLY DRIVEN CONTINUOUS FLOW CENTRIFUGE".

The flexible processing/expressor bags according to embodiments of the present invention may be made of natural or synthetic material, in one or more layers or combined in one or more layers with other known materials. In that regard, embodiments of the present invention are preferably manufactured of a plastic material and sterilized prior to use.

The expandable wall incorporated into some of the embodiments of the present invention allow a processing and/or expressor bag to have an increased and/or variable volume capacity. Specifically, a processing/expressor bag 500 may include a plurality of assembled pairs 502 of wall partitions 502a, 502b.

Having now described some of the embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention. The contents of any references cited throughout this application are hereby incorporated by reference. The appropriate components, processes, and methods of those documents may be selected for the present invention and embodiments thereof.

What is claimed is:

1. A flexible centrifuge chamber comprising:
   a substantially flexible first side having a centrally located flattened annulus defining an axial opening;
   a substantially flexible second side having a centrally located flattened annulus defining an axial opening; and
   an expandable wall, wherein a first end of the expandable wall is attached to a circumference of the first side of the flexible chamber and a second end of the expandable wall is attached to a circumference of the second side of the flexible chamber, wherein the expandable wall comprises an accordion wall having substantially no rigid portions; and wherein the chamber is sterilized.

2. The flexible chamber according to claim 1, wherein the chamber comprises a processing chamber.

3. The flexible chamber according to claim 1, wherein the chamber comprises an expressor chamber.

4. The flexible chamber according to claim 1, wherein the expandable accordion wall includes at least one pair of corresponding connected flaps, wherein a first flap of the pair of flaps includes a first circumferential end attached to the circumference of the first side of the flexible chamber and wherein a second flap of the pair of flaps includes a second circumferential end attached to the circumference of the second side of the flexible chamber.

5. The flexible chamber according to claim 4, wherein the expandable accordion wall includes a plurality of pairs of flaps.

6. A processing apparatus for a continuous flow centrifuge, comprising:
   a flexible chamber comprising:
      a substantially flexible first side having a centrally located flattened annulus defining an axial opening;
      a substantially flexible second side having a centrally located flattened annulus defining an axial opening; and
      a circumferential expandable wall, wherein a first end of the expandable wall is attached to a circumference of the first side of the flexible chamber and a second end of the expandable wall is attached to a circumference of the second side of the flexible chamber, wherein the expandable wall comprises an accordion wall having substantially no rigid portions; and wherein the chamber is sterilized.

7. The processing apparatus according to claim 6, wherein the expandable accordion wall includes at least one pair of corresponding connected flaps, wherein a first flap of the pair of flaps includes a first circumferential end attached to the circumference of the first side of the flexible chamber and wherein a second flap of the pair of flaps includes a second circumferential end attached to the circumference of the second side of the flexible chamber.

8. The processing apparatus according to claim 7, wherein the expandable accordion wall includes a plurality of pairs of flaps.

9. The processing apparatus according to claim 6, wherein the flexible chamber comprises a processing chamber for containing a material to be centrifuged.

10. The processing apparatus according to claim 6, wherein the flexible chamber comprises an expressor chamber for containing an expressor material.

11. The processing apparatus according to claim 6, further comprising a plurality of flexible chambers.

12. The processing apparatus according to claim 11, wherein one or more of the plurality of flexible chambers comprise processing chambers for containing material to centrifuge and one or more of the plurality of flexible chambers comprise expressor chambers for containing expressor material.

13. A continuous flow centrifuge including:
a plurality of flexible chambers, each comprising:
a substantially flexible first side having a centrally located flattened annulus defining an axial opening; and
a substantially flexible second side having a centrally located flattened annulus defining an axial opening, the flexible chamber further comprising:
a circumferential expandable wall, wherein a first end of the expandable wall is attached to a circumference of the first side of the flexible chamber and a second end of the expandable wall is attached to a circumference of the second side of the flexible chamber,
wherein the expandable wall comprises an accordion wall having substantially no rigid portions; and
wherein the chamber is sterilized.

14. A biological cell processing apparatus comprising:
a continuous flow centrifuge; and
a flexible chamber comprising:
a substantially flexible first side having a centrally located flattened annulus defining an axial opening;
substantially flexible second side having a centrally located flattened annulus defining an axial opening; and
a circumferential expandable wall,
wherein a first end of the expandable wall is attached to a circumference of the first side of the flexible chamber and a second end of the expandable wall is attached to a circumference of the second side of the flexible chamber,
wherein the expandable wall comprises an accordion wall having substantially no rigid portions; and
wherein the chamber is sterilized.

15. The flexible chamber according to claim 1, wherein the circumference of each of the first and second sides circumscribes the respective axial opening.

16. The processing apparatus according to claim 6, wherein the circumference of each of the first and second sides circumscribes the respective axial opening.

17. The continuous flow centrifuge according to claim 13, wherein the circumference of each of the flexible first and second sides circumscribes the respective axial opening.

18. The biological cell processing apparatus according to claim 14, wherein the circumference of each of the flexible first and second sides circumscribes the respective axial opening.

* * * * *